United States Patent [19]

Schumacher et al.

[11] Patent Number: 4,480,463

[45] Date of Patent: Nov. 6, 1984

[54] PROCESS FOR DETERMINING THE RESISTANCE TO DRAW AND THE GAS PERMEABILITY OF A TEST PIECE AND A DEVICE FOR CARRYING OUT SUCH A PROCESS

[75] Inventors: Gerd Schumacher, Pinneberg-Waldenau; Heinz-Werner Masurat, Pinneberg, both of Fed. Rep. of Germany

[73] Assignee: B.A.T. Cigaretten-Fabriken GmbH, Hamburg, Fed. Rep. of Germany

[21] Appl. No.: 359,913

[22] Filed: Mar. 19, 1982

[30] Foreign Application Priority Data

Mar. 23, 1981 [DE] Fed. Rep. of Germany ....... 3111318

[51] Int. Cl.$^3$ ............................................. G01N 15/08
[52] U.S. Cl. ........................................................ 73/38
[58] Field of Search ............................ 73/38, 37.7, 37

[56] References Cited

U.S. PATENT DOCUMENTS

| | | | |
|---|---|---|---|
| 3,991,605 | 11/1976 | Reuland | 73/38 |
| 4,177,670 | 12/1979 | Heitmann et al. | 73/38 |
| 4,191,046 | 3/1980 | Baker et al. | 73/38 |
| 4,198,853 | 4/1980 | Graham et al. | 73/38 |
| 4,198,854 | 4/1980 | Washington et al. | 73/38 |
| 4,223,551 | 9/1980 | Greve et al. | 73/38 |
| 4,227,397 | 3/1979 | Neri | 73/38 |

FOREIGN PATENT DOCUMENTS

| | | |
|---|---|---|
| 2828430 | 2/1979 | Fed. Rep. of Germany . |
| 2847786 | 5/1979 | Fed. Rep. of Germany . |
| 2949200 | 6/1980 | Fed. Rep. of Germany . |
| 2074735 | 12/1981 | United Kingdom ................ 73/38 |

*Primary Examiner*—Gerald Goldberg
*Assistant Examiner*—Hezron E. Williams
*Attorney, Agent, or Firm*—Finnegan, Henderson, Farabow, Garrett & Dunner

[57] ABSTRACT

In a process for determining the resistance to draw and the gas permeability of a test piece, for example a cigarette or a cigarette paper, a linearly increasing or decreasing volumetric flow is conveyed through the test piece. The volumetric flow and the pressure drop at the test piece are measured continuously and compared with predetermined reference values. When there is equality between at least one measured value and a reference value, the measured value pair under consideration, volumetric flow/pressure drop, is detected. It is thus possible, on the one hand, to determine the characteristic curve of the test piece, i.e. the change in the pressure drop with the volumetric flow, over a greater range of the volumetric flow, and, on the other hand, to measure pairs of values for accurately defined values of the volumetric flow and/or the pressure drop.

15 Claims, 3 Drawing Figures

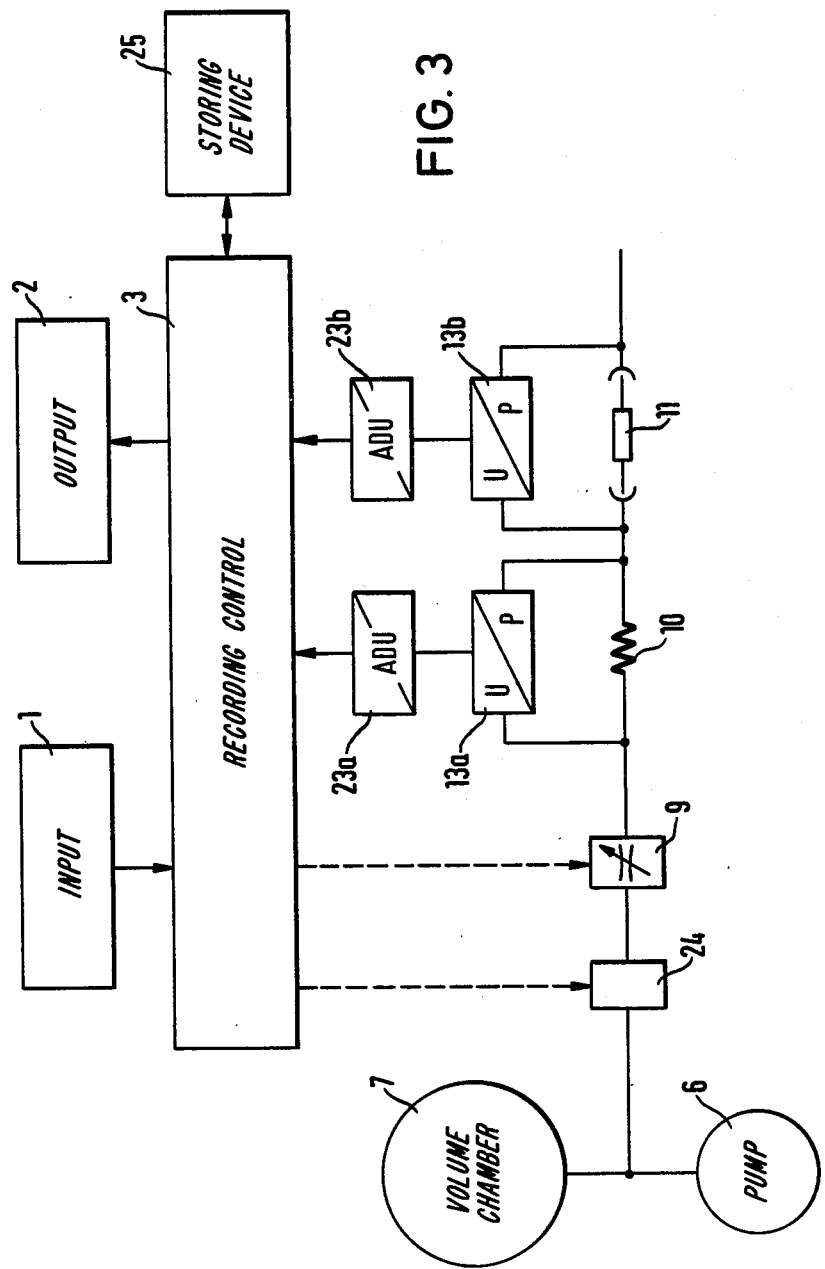

PROCESS FOR DETERMINING THE RESISTANCE TO DRAW AND THE GAS PERMEABILITY OF A TEST PIECE AND A DEVICE FOR CARRYING OUT SUCH A PROCESS

FIELD OF THE INVENTION

The invention relates to a process for determining the resistance to draw and gas permeability of a test piece as well as a device for carrying out such a process.

BACKGROUND OF THE INVENTION

The difficulties arising here will be described below with reference to the determination of the gas permeability of papers for the production of cigarettes on the one hand and the determination of the resistance to draw of cigarettes and filter rods on the other hand.

According to the draft of German Standard DIN 10251 of July, 1980, the static pressure difference between the two ends of the sample is designated as the resistance to draw of a cigarette or a filter rod if the sample is permeated by an airstream of 17.5 ml/s, measured at the outlet end, under constant conditions.

According to the draft of the International Standard ISO 2965-1979 published by the International Organisation for Standardisation, the air permeability of cigarette paper is defined as a ratio between the volumetric flow of air per unit area of the test material and the pressure difference between the two sides of the test material.

Various apparatuses for determining either the air permeability or the resistance to draw have been developed.

Thus, German Offenlegungsschrift No. 2 949200 discloses a device for determining the air permeability of cigarette paper in which several flow passages are arranged between the source of the volumetric flow and the test piece, which can be arranged in such a way as to alter the flow conditions. However, this results in a relatively complicated structure.

Furthermore, German Offenlegungsschrift No. 2 847 786 describes a process for determining the air permeability of cigarette or filter paper in which the volumetric flow through the test piece is adjusted to various values situated in the vicinity of a set value, thus for example at 17.5 ml/s. The respective pressure drop is then measured at the various adjusted values and the air permeability in turn calculated from the various measured values. Alternatively, various values in the vicinity of a predetermined pressure drop, thus for example 1 kPa, can be measured with the associated volumetric flows and the air permeability calculated therefrom. With this process, however, the air permeability can only be determined approximately for a specific volumetric flow or a specific pressure drop, by forming a mean value.

Finally, German Offenlegungsschrift No. 2 828 430 describes another device for determining the air permeability of cigarette paper in which the air is sucked through the cigarette paper via three different paths of flow which can each be sealed by valves. The path of flow permitting manual adjustment of the desired value must be determined in the first instance as a function of the air permeability of the cigarette paper. Only then can actual measurement take place.

Moreover, the known processes all have the limitation that they are specifically intended only for determining the air permeability of cigarette paper, the determination of the resistance to draw not being claimed.

SUMMARY OF THE INVENTION

The object of the invention is therefore to propose an easily manageable and, at the same time, accurate process for determining the resistance to draw and the gas permeability of a test piece of the type indicated and a device for carrying out such a process, in which the above-mentioned disadvantages do not arise.

In particular, the description contained herein will define a process and a device with which it is possible to determine both the resistance to draw and the gas permeability of test pieces very accurately and reproducibly.

The objects of the process are achieved according to the invention by the features specified in claim 1.

The objects of the device are achieved according to the invention by the features specified in claim 2.

The advantages achieved with the invention are due to the mode of operation described hereinafter. A volumetric flow, which is produced by a special source, discussed herein, permeates the available flow region in the course of a specific time, causing a linear change in the flow. Thus, the volumetric flow essentially relates to the passage of a pressurized gaseous medium through a test piece, such as filter paper, which constitutes a flow resistance. If a certain pressure difference or pressure drop is maintained between the two ends of the test piece, a definite volume of gas, the volumetric flow, can flow through the test piece. As the variable volumetric flow is conveyed through the test piece, the volumetric flow and the pressure drop over the test piece are measured continuously in the test piece. The available test results, i.e. the instantaneous values of volumetric flow and pressure drop over the test piece are compared with programmed reference values. As soon as at least one instantaneous value coincides with a reference value, the appropriate instantaneous value pair, volumetric flow/pressure drop over the test piece is detected.

The characteristic curve of the test piece, which is defined by the relationship between the permeating volumetric flow and the pressure drop over the test piece is obtained over a greater range of flow volumes than disclosed in the prior art. Further the two relevant measured values, namely the pressure drop and the volumetric flow, can be determined and used to compute accurately the resistance to draw and the gas permeability of the test piece, for example, this can be accomplished with an airstream of 17.5 ml/s or a pressure drop of 1 kPa, as required in the draft of German Standard DIN 10251 or International Standard ISO 2965.

Therefore, if the gas permeability and the resistance to draw in certain tobacco products, such as particular cigarettes and filter rods, are to be investigated, it is necessary only to fix a suitable test piece, such as a cigarette and a cigarette holder. The test piece is then attached to the measuring device so that the characteristic curve of the cigarette, that is, the values used in calculating gas permeability and resistance to draw of the test piece, are produced by the procedure described above.

When the gas permeability and resistance to draw of cigarette paper, filter paper or tipping paper is to be determined, the cigarette holder is replaced by a gripping device for the paper. The ratio between the volumetric flow of air per unit area of the test material and the pressure difference between the two sides of the test material are detected. As a result, the air permeability of the paper is determined, using the same measuring process, as with a cigarette or filter rod, but with a different support device for the test piece.

By predetermining certain reference values, it is possible to ensure that the appropriate instantaneous values of the pressure drop and the volumetric flow are also actually detected.

According to a preferred embodiment, the source of the linearly increasing or decreasing volumetric flow comprises a pump generating a pressure which is reduced relative to atmospheric pressure within a volume chamber. Between the test piece and the junction between pump and volume there is located a valve controlled by a motor so that a variable volumetric flow can be delivered.

Alternatively, a sawtooth oscillator which adjusts the value via a control card and thus delivers a continually varying volumetric flow can be provided.

The volumetric flow is preferably measured by determining the pressure drop at a linear flow resistance, i.e. in such a way that two pressure measurements have to be made. The results of the two pressure measurements are preferably converted into digital values so that further processing can be effected by a digital computer.

In order to reduce the structural costs, it is preferable to provide only a single comparator which is connected selectively to one of the two pressure gauges, only one of the respective appropriate instantaneous values for the two variables being compared with the associated reference value.

This comparator is connected to scanning and holding members capable of displaying the instantaneous values of all variables when there is equality between an instantaneous value and its associated reference value.

It is also possible to provide a recorder which records the two measured variables, namely the volumetric flow and the pressure drop, as a function of time.

It is preferable to provide an additional valve in the flow source in order to adjust the reduced pressure in the volume chamber and thus the maximum flow volume at a given total flow resistance.

BRIEF DESCRIPTION OF THE DRAWINGS

The invention is described in more detail below by means of reference to the attached schematic drawings.

FIG. 3 shows a basic circuit diagram of a program controlled measured value detecting and control system.

Figure 1:
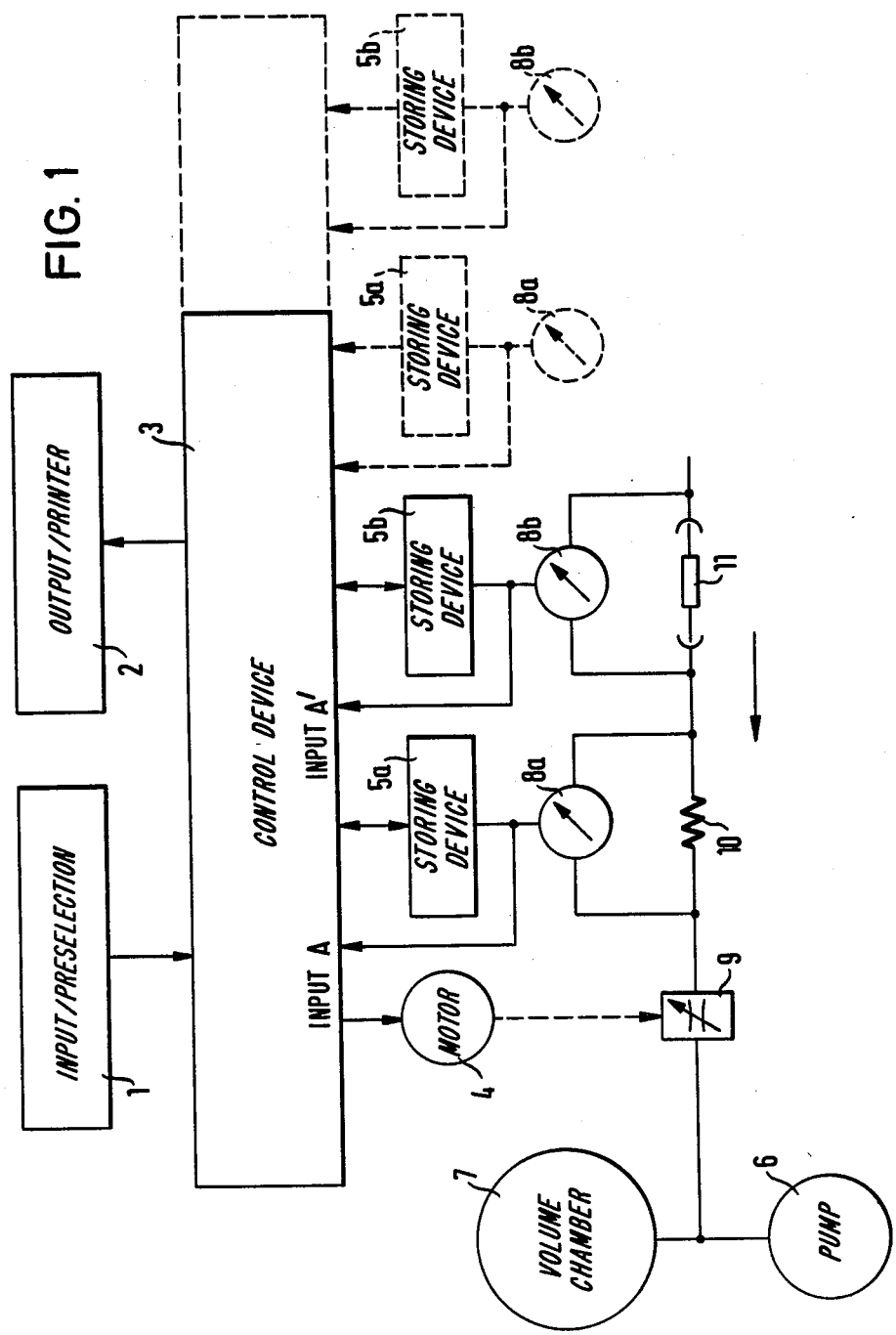
FIG. 1 shows a block circuit diagram of the theoretical structure of a device for determining the flow resistance and the gas permeability of the test piece.

The same respective reference numerals are used for the same structural elements in the following description. Further, test piece 11 can be cigarette, filter as well as tipping paper or a cigarette or a filter rod.

FIG. 1 shows the basic principle of such a device. In this arrangement, a pump 6 generates a pressure which is reduced relative to atmospheric pressure in a volume chamber 7. A corresponding reduced pressure dependent on the pressure drop over the flow path is applied via an adjustable valve 9 at a connection for a holder for a test piece 11 which is open to the atmosphere on its other side. The valve 9 is controlled via a motor 4 so that a variable volumetric flow passes through the test piece 11 in the direction of the arrow. Numerals 6, 7, and 9 constitute the source of the linearly changing volumetric flow.

Between the valve 9 and the test piece 11 there are located a flow meter comprising a linear flow resistance 10 and a differential pressure transmitter 8A. A pressure drop occurs at linear flow resistance 10 which is measured by means of the differential pressure transmitter 8A. A corresponding differential pressure transmitter 8b determines the pressure drop at the test piece 11.

The pressure drop at the linear flow resistance 10 is proportional to the volumetric flow so the volumetric flow can be determined by measuring this change in pressure. From this calculation, gas permeability of the test piece is determined, whereas the pressure drop measured by 8b allows resistance to draw to be determined. As shown by the arrow in FIG. 1, this arrangement of elements permits continuous computation of resistance to draw and gas permeability in the same test process.

The differential pressure transmitters 8a and 8b convert the determined pressure into corresponding electrical signals, the electrical value for the volumetric flow being transmitted from the differential pressure transmitter 8a to the input A and the electrical value for the pressure drop at the test piece 11 being transmitted to an input A' of a control device 3.

In addition, these two electrical variables are transmitted to stores 5a and 5b which determine the instantaneous value of the two electrical variables as soon as at least one variable, for example the independent variable, i.e. the volumetric flow, corresponds to a predetermined reference value.

These reference values can be transmitted via an input unit 1 to the control unit 3 which also contains an arithmetic unit and performs the comparison between the measured instantaneous values and the indicated reference values.

As soon as equality between at least one of the reference values and the appropriate instantaneous value is determined, the stores 5a and 5b are controlled so that the appropriate instantaneous values are detected, transmitted to the control unit 3 and emitted via an output unit 2, for example a printer.

FIG. 1 shows additional stores 5a and 5b as well as differential pressure transmitters 8a and 8b which can be used for a different measuring device (not shown) which operates by the same principle, as the control and evaluation take place centrally via the arithmetic unit 3.

The motor 4 for adjusting the valve 9 is also adjusted via the control unit 3, so that the control unit administers the various units centrally.

Figure 2:
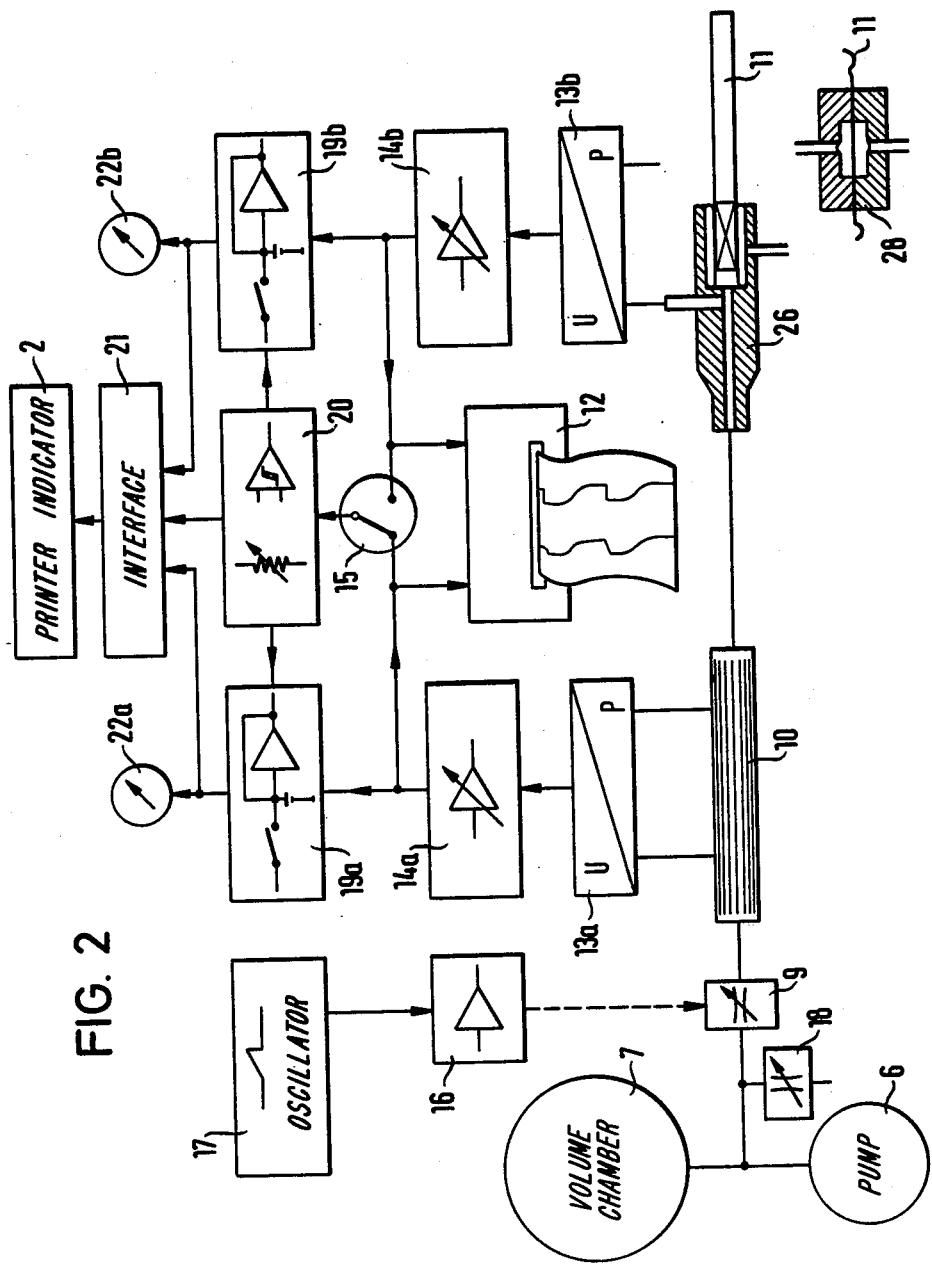
FIG. 2 shows the detailed structure of the embodiment shown in FIG. 1.

FIG. 2 shows an embodiment in which the central control unit has been omitted. The actual measuring head is shown in detail. If the gas permeability and resistance to draw of cigarettes or filter rods is to be determined, one end of the test piece 11, i.e. of the cigarette or the filter rod, is gripped in a holder 26 which is connected via the linear flow resistance 10 to the source 6,7,9 for the linearly increasing or decreasing gas stream. The part of the cigarette 11 not fixed in the holder is exposed to the atmosphere.

If the air permeability of cigarette, filter or tipping paper is to be measured, this paper is gripped in the manner shown in FIG. 2 between two clamping jaws of a holder 28, of which one side is attached via the flow resistance 10 to the source 6,7,9 and the other side is exposed to the atmosphere.

A second valve 18 with which the reduced pressure in the volume 7 and therefore the maximum flow volume can be adjusted at a given total flow resistance is located between the valve 9 and the junction between the pump 6 and the volume 7.

The differential pressure occurring at the linear flow resistance 10 and at the test piece 11 is detected via a pressure pick-up 13a and 13b, respectively, which generates an electrical signals proportional to the differential pressure corresponding to the volumetric flow and to the pressure drop at the test piece. The signals are amplified by means of amplifiers 14a and 14b. These amplifiers 14a and 14b permit quantitative adaptation of the electrical variables to the measured variables.

A recorder 12 which is connected downstream of the amplifiers 14a and 14b records the two measured variables as a function of time.

The output signals from the two amplifiers 14a, 14b are also transmitted via a switch 15 to a comparator 20 and also to scanning and holding members 19a, 19b which are controlled by the comparator 20.

The comparator compares selectively one of the two instantaneous values under consideration for the pressure drop or the volumetric flow with predetermined reference values and, when there is equality between a reference value and any measured value, emits an output signal to the scanning and holding members 19a and 19b, which then retain the instantaneous values of volumetric flow and change in pressure over the test piece.

The measured values detected in this way are displayed by separate display units 22a, 22b.

An interface 21 which is connected downstream of the scanning and holding members 19a, 19b as well as the comparator 20 processes the measured values, for example performs analog/digital conversion, and transmits the processed measured values to an output unit 2, for example a printer or a display unit.

In this embodiment, the analog wave 9 is adjusted by means of a control card 16 which is controlled by a sawtooth generator 17. The analog wave thus opens and closes continuously to generate the above-mentioned linearly increasing or decreasing volumetric flow.

FIG. 3 shows the principle of a program-controlled measured value detecting and control system, and it is possible, for example, to use the microprocessor Z80 in the programme control unit 3.

The path of the flow from the atmosphere via the test piece to the source has essentially the structure described already with reference to FIG. 1, but an adjustable pressure regulator 24 is arranged between the valve 9 and the junction between pump 6 and volume chamber 7 to limit the available region.

The electrical signals generated by the two pressure pick-ups 13a, 13b are converted in analog/digital converters 23a, 23b into corresponding digital signals, which are fed to the control unit 3.

The control unit 3 is connected to a central store 25 containing the predetermined reference values which are compared in the control unit 3 with the instantaneous values for the volumetric flow and the pressure drop. When there is equality between at least one reference value and the measured values for either volumetric flow or change in pressure over the test piece, the instantaneous value pair under consideration is displayed or delivered via the output unit 2.

Any number of points of support in the characteristic curve of a paper or a smokeable article or filter rod can be detected by the method described herein, so such a characteristic curve can be determined very accurately. The number of points of support at a given change in volumetric flow per unit time is limited only by electrical variables, in particular by the conversion rate of the analog/digital converter and by the time for feeding the measured values into the store.

In addition to the improved means for determining the gas permeability and resistance to draw described herein, the device can also be used for determining the secondary air content, for example the ventilation, of smokeable article. It can also be used to compute a different variable which changes with a variation in the volumetric flow.

We claim:
1. A process for determining the resistance to draw and the gas permeability of a test piece in which an adjustable quantity of gas is conveyed through the test piece and the volumetric gas flow as well as the change in pressure across the test piece are measured, comprising the steps of:
   (a) conveying a linearly increasing or decreasing gas flow through the test piece;
   (b) measuring continuously the resultant changes in gas flow and pressure across the test piece and comparing the measured values with predetermined reference values; and
   (c) determining instantaneous values for gas flow and change in pressure across the test piece when there is equality between at least one measured value and any predetermined reference value, wherein the measurement of gas flow enables a determination of gas permeability and the measurement of change in pressure across the test piece enables a determination of resistance to draw.

2. A device for determining the resistance to draw and the gas permeability of a test piece comprising a source producing an adjustable volumetric gas flow, a support for the test piece, said support being connected with said source, a flow meter for generating continuously measured values corresponding to the volumetric flow of said gas, a first pressure gauge for measuring continuously the change in pressure across the test piece and an evaluating device, wherein said evaluating device further includes a memory containing predetermined reference values, a comparator for comparing the measured values for gas flow and change in pressure across the test piece with the predetermined reference values, and means for detecting instantaneous values for both gas flow and change in pressure across the test piece when equality exists between any predetermined reference value and any measured values corresponding either to gas flow or to change in pressure across said test piece, wherein the measurement of gas flow enables a determination of gas permeability and the measurement of change in pressure across the test piece enables a determination of resistance to draw, and wherein said source creates a linearly increasing or decreasing gas flow.

3. A device according to claim 2, wherein said source acts upon one side of the test piece and comprises a pump, a volume, an adjustable valve, wherein said pump generates in said volume a subatmospheric pressure, and said adjustable valve is connected to the pump and the volume and to the test piece.

4. A device according to claim 3, wherein said adjustable valve is connected to a junction between the pump and the volume.

5. A device according to claim 4, wherein said flow meter comprises a second valve connected between said adjustable valve and said junction between the pump and the volume, whereby the maximum flow volume against total flow resistance is adjusted.

6. A device according to claim 5, wherein said flow meter comprises a linear flow resistance and a second pressure gauge, wherein said linear flow resistance is positioned between the source and the test piece, and said second pressure gauge measures the pressure drop across the linear flow resistance.

7. A device according to claim 6, wherein said memory stores said predetermined reference values for comparison with said measured values detected at said first and second pressure gauges.

8. A device according to claim 7, also including a change-over switch, said change-over switch connecting the comparator selectively with either the first or second pressure gauges.

9. A device according to claim 8, also including scanning and holding members wherein the scanning and holding members are connected with the comparator and the first and second pressure gauges.

10. A device according to claim 9, also including two analog to digital converters, wherein each converter is positioned between an individual pressure gauge and the evaluating device, and whereby the processing and evaluation is performed digitally.

11. A device according to claim 10, having a recorder wherein the recorder continuously records values for gas permeability and resistance to draw as a function of time.

12. A device according to claim 11, further comprising two separate display units for displaying the continuously recorded values.

13. A device to any one of claims 3 to 12 also including a motor wherein the motor adjusts the adjustable valve.

14. A device according to claim 13, wherein the motor is controlled by the evaluating device.

15. A device according to any one of claims 3 to 12, also including a saw-tooth generator and a control card wherein said saw-tooth generator adjusts the adjustable valve via the control card.

* * * * *